United States Patent [19]

Yoon

[11] 4,103,680
[45] Aug. 1, 1978

[54] MULTIPLE OCCLUSION RING APPLICATOR AND METHOD

[76] Inventor: In Bae Yoon, 2213 Forest Ridge Rd., Timonium, Md. 21093

[21] Appl. No.: 605,197

[22] Filed: Aug. 15, 1975

Related U.S. Application Data

[60] Continuation-in-part of Ser. No. 605,217, Aug. 15, 1975, which is a continuation-in-part of Ser. No. 518,617, Oct. 29, 1974, Pat. No. 3,989,049, which is a division of Ser. No. 383,475, Jul. 30, 1973, Pat. No. 3,870,048.

[51] Int. Cl.² .................. A61B 17/12; A61B 17/22
[52] U.S. Cl. .................. 128/6; 128/303 A; 128/303.15; 128/326
[58] Field of Search ............. 128/303 A, 303.15, 325, 128/326, 327, 6

[56] References Cited

U.S. PATENT DOCUMENTS

| | | | |
|---|---|---|---|
| 1,400,653 | 12/1921 | Barbour | 128/326 UX |
| 2,371,082 | 3/1945 | Vistreich | 128/325 |
| 3,687,138 | 8/1972 | Jarvik | 128/326 |
| 3,760,810 | 9/1973 | Van Hoorn | 128/303 A X |
| 3,870,048 | 3/1975 | Yoon | 128/303 A X |

*Primary Examiner*—Robert W. Michell
*Assistant Examiner*—Michael H. Thaler
*Attorney, Agent, or Firm*—Finnegan, Henderson, Farabow & Garrett

[57] ABSTRACT

A multiple ring applicator device and method for applying elastic occluding rings to an anatomical tubular structure which comprises a laparoscope which contains a ring applicator device integral therewith, the ring applicator device and the laparoscope cooperating to effect the application of multiple elastic occluding rings to the tubular structures without the necessity of removing the ring applicator device from the patient's body for reloading purposes.

25 Claims, 11 Drawing Figures

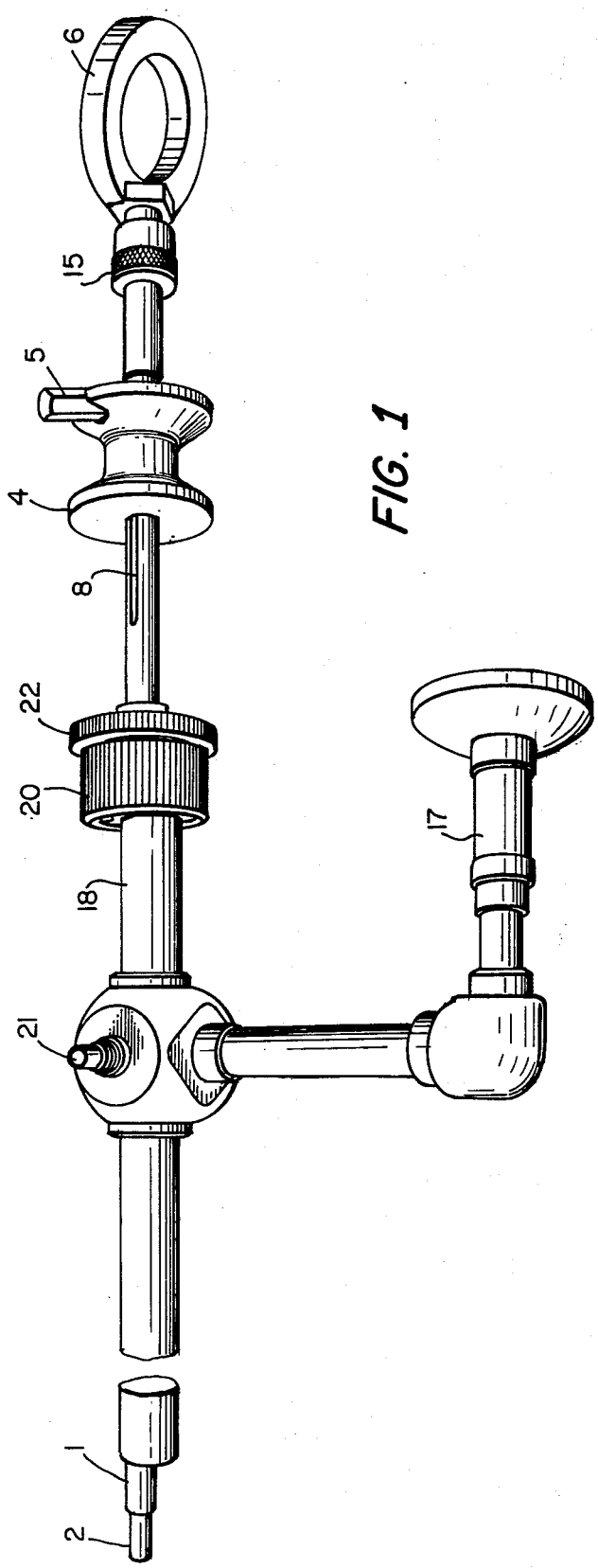

MULTIPLE OCCLUSION RING APPLICATOR AND METHOD

BACKGROUND OF THE INVENTION

The present application is a continuation-in-part application of an application entitled "An Occlusion Ring Applicator and Method", Ser. No. 605,217 filed on Aug. 15, 1975 which is a continuation-in-part application of Ser. No. 518,617, filed on Oct. 29, 1974, now U.S. Pat. No. 3,989,049 issued on Nov. 2, 1976, which is a division of Ser. No. 383,475 filed on July 30, 1973, now U.S. Pat. No. 3,870,048 issued on Mar. 11, 1975. The subject matter of said application is hereby incorporated into the present application by reference.

The present invention relates to a multiple occlusion ring applicator device and method for applying a plurality of elastic occluding rings to an anatomical tubular structure. More particularly, the present invention is directed to a ring applicator device which is operatively associated with an optical viewing means and the illuminating means for effecting the ligature of both of the Fallopian tubes without the necessity of removing the instrument from the patient for the purpose of reloading the instrument. The device and method of the present invention is effective for carrying out the tubal ligation of the human female in order to effect temporary or permanent sterilization. The device and method of the present invention can also be utilized effectively to sterilize the human male.

In many areas of the world, the question of population control has become a central issue. Since birth control devices are not always used faithfully or fail to work in some instances, various procedures have been proposed for effecting the sterilization of women as well as men. However, many of these techniques are unpopular because of the resulting complications, the high expense and because of the general unacceptability among the populace of effecting a sterilization which is permanent and cannot be reversed. Nevertheless, sterilization is obviously an effective means for solving various problems of population explosion and of voluntarily limiting the size of the family, where desired, on the part of the parent. Accordingly, research into finding various techniques and instruments has continued both under private and government support.

Tubal ligation has commonly been used to effect sterilization in women. The common practice is to cut and tie the Fallopian tubes in order to prevent fertilization of the egg. More recently, the use of clips for closing the tubes has been suggested. Another recent procedure involves cauterization of the tubes by electrical means. However, each of these procedures involves much discomfort to the patient, and highly skilled personnel are required to complete the operation successfully. Also, in the procedure requiring the use of clips, in some instances the clips have fallen off, thereby rendering the sterilization ineffective. With respect to cauterization by means of electricity, there remains the ever-present dangers of inadvertently burning certain organs of the body and, for example, accidentally rupturing the bowel.

In the recently developed ring applicator devices wherein the Fallopian tubes are ligated by an elastic ring, many of the abovementioned difficulties have been eliminated. However, most of said ring applicator devices are capable of ligating only one Fallopian tube at a time. Thus, in such devices, after one of the Fallopian tubes has been occluded by placing an elastic ring around a knuckle formed in said Fallopian tube, it is then necessary to completely withdraw the instrument from the patient and reload the instrument with another elastic ring for ligating the second Fallopian tube. Such a technique is not only time-consuming, but also unduly complicates the tubal ligation procedure and, in some instances, can increase the ever possible chance of infection.

SUMMARY OF THE INVENTION

One of the objects of the present invention is to provide a simplified instrument and method for applying at least one occluding ring to an anatomical tubular structure.

Another object of the present invention is to provide a simplified instrument and method for effecting permanent or temporary sterilization of the human female.

A further object of the present invention is to provide a novel technique and instrument for accomplishing tubal ligation which may be employed by a physician with many degrees of skill and without the need of expensive or bulky equipment.

A still further object of the present invention is to provide a portable instrument for mechanically effecting tubal ligation wherein the grasping of the reproductive tubular member and effecting the release of one of the elastic rings around a knuckle (bend) formed in the tubular member to occlude it can be achieved through a simple manipulation of a ring applicator device utilizing only one hand.

An additional further object of the present invention is to provide a ring applicator device which is physically combined with an endoscopic system in such a way as to enable the physician operating the device to view the entire ligation operation.

Yet another object of the present invention is to provide a multiple ring applicator device which is combined with an endoscopic system to produce an instrument which is effective in ligating both of the Fallopian tubes of a female upon a single entry of the instrument into the body of the patient and without the necessity of reloading the device.

A still further object of the present invention is to provide a ring applicator device which can be connected to a source of electrical current for electrically charging the grasping forceps.

Yet another object of the present invention is to provide an endoscopic system, for example, a laparoscope which is combined with a multiple ring applicator device in such a manner as to substantially eliminate the possible contamination of the instrument or the physician's hand.

Still another object of the present invention is to provide an instrument which can also be used for the temporary or permanent sterilization of the human male.

Other objects and further scope of applicability of the present invention will become apparent from the detailed description given hereinafter; it should be understood, however, that the detailed description and specific examples, while indicating preferred embodiments of the invention, are given by way of illustration only, since various changes and modifications within the spirit and scope of the invention will become apparent to those skilled in the art from this detailed description.

Pursuant to the present invention, the above-mentioned disadvantages may be eliminated and an improved ligature method and ring applicator device may be obtained by following the teachings of the present invention.

In accordance with the present invention, the sterilization of the human male or the human female may be obtained by the use of elastic rings for effecting a ligature in said reproductive tubular member. Advantageously, the ligature is performed in conjunction with an endoscopic system, for example, a laparoscope, which is a device well known in the medical field for viewing the internal portions of the body.

The instrument of the present invention comprises a ring applicator which is combined with an endoscope, said ring applicator and endoscope cooperating to effect the ligature of both of the Fallopian tubes of a female upon a single entry of the instrument into the body without the need of reloading the device. The ring applicator device comprises a grasping means which is used to pull a portion of the Fallopian tube of the female into the device, thereby forming a knuckle or a bed in the Fallopian tube, and slidable cylinder means for slipping or pushing the elastic or stretchable ring over the portion of the Fallopian tube held in the device, thereby effecting the ligature.

In operation, a ring applicator device containing an inner and outer cylinder is physically combined with an endoscopic system, for example, the operating channel of a laparoscope, so that the front end portion of the ring applicator device extends beyond the front end portion of the laparoscope. Then, an elastic ring is mounted on both the outside and inside cylinders of the ring applicator device.

A natural body entrance is then selected near the tubular member to be ligated. In the case of performing the sterilization of the human female, the natural body entrance would be either through the abdominal wall or through the vagina, depending upon the option of the physician. Since the ring applicator could also be used for shortening various ligaments by forming a knuckle therein, the natural body entrance would be selected near the particular tubular member which is desired to be shortened. In the next step of the method, entry is obtained through said natural body entrance by standard medical procedure. For example, when it is desired to ligate the Fallopian tubes, entrance through the abdominal wall may be obtained by making a small incision in the navel area. Because the ring applicator device is disposed in the operating channel of a laparoscope, only one incision is necessary through the abdominal wall. In the next step, the laparoscope containing the ring applicator device is inserted through said entrance to the location area of said tubular member. Then the grasping means is pushed forward to engage a segment of the first Fallopian tube. The grasping means is then retracted into the inner cylinder of the ring applicator device a sufficient distance to form a knuckle or bend in the Fallopian tube and then the release of the elastic ring disposed on the inner cylinder is effected around the knuckle in the Fallopian tube, thereby occluding it. The grasping means can then be released to free the occluded portion of the Fallopian tube from the ring applicator device, leaving a ligatured Fallopian tube. Then, while the instrument is still in position, the ring applicator is axially retracted within the operating channel provided in the laparoscope until the proximal end of the laparoscope pushes the elastic ring disposed on the outer cylinder onto the inner cylinder. The ring applicator device is then repositioned within the operating channel of the laparoscope and the instrument is now ready for the ligature of the second Fallopian tube. The same procedure for ligating the first Fallopian tube is then repeated in order to ligate the second Fallopian tube.

After the ring applicator device has been withdrawn from the body entrance, the entry made through the use of medical procedure is closed where applicable. If desired, the knuckles held by the elastic rings can be cut by the edges of the grasping means in order to effect permanent sterilization. Alternatively, the knuckles can be left as is with the elastic rings holding the Fallopian tubes in a crimped position, thereby temporarily or permenently effecting sterilization. Temporary sterilization is contemplated by using an elastic ring which is sufficient to effect a ligature of the Fallopian tube, but is not so strong as to cut off the blood supply through the walls of the Fallopian tube. When temporary sterilization is envisioned, the elastic rings can be removed from the Fallopian tubes in a subsequent operative procedure.

In the method and device of the present invention, the grasping of the reproductive tubular member by the ring applicator device and applying an elastic ring to a knuckle formed in the tubular member is accomplished by a single manipulation of the ring applicator device utilizing only one hand of the physician. Thus, after the tubular structure has been grasped by the grasping means, by withdrawing an operating slide by the fore and middle fingers in the rearward direction of the device, not only is the tubular structure drawn into the inner cylinder of the ring applicator, but also through the continual rearward operation of the operating slide, the inner cylinder is drawn within the outer cylinder, thereby displacing the elastic ring from the distal end of the ring applicator device. Thus, by one continuous rearward action of the operating slide, a knuckle is formed in the tubular member and said tubular member is ligated with an elastic ring.

One of the most advantageous features of the present invention is that by providing a proper cooperation of the laparoscope with the ring applicator device, the instrument becomes a multiple ring applicator which can achieve the ligature of both of the Fallopian tubes upon a single entry of the instrument into the body without the need of reloading the device.

Another feature of the present invention comprises a means for selectively charging the grasping means with an electrical current. Thus, if desired, the grasping means can be used to electrically sever and cauterize the Fallopian tubes, repair lesions, or perform any other type of procedure which would require an electrical current.

BRIEF DESCRIPTION OF THE DRAWINGS

The present invention will become more fully understood from the detailed description given hereinbelow and the accompanying drawings which are given by way of illustration only, and thus are not limitative of the present invention, and wherein, FIG. 1 illustrates a perspective view of the ring applicator device of the present invention in combination with a laparoscope;

FIGS. 4A and 4B show two different embodiments of the forceps means utilized in the present invention, particularly when an electrical current is introduced to said forceps means.

DETAILED DESCRIPTION OF THE DRAWINGS

Figure 2:
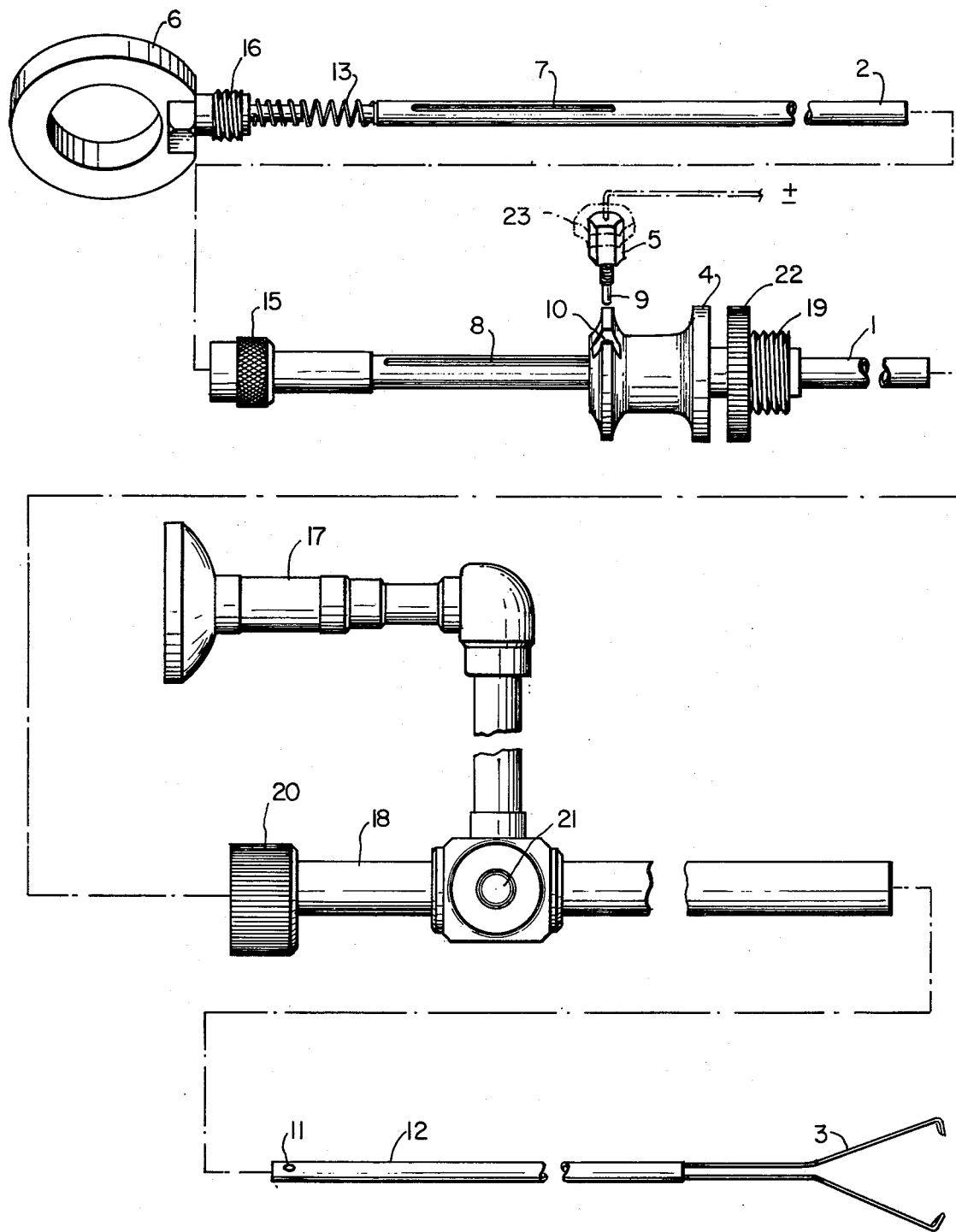
FIG. 2 shows the ring applicator device of FIG. 1 in a disassembled state.

In the following description of the figures, like numerals are used throughout the various views to indicate like elements. The device of the present invention comprises an inner tube or cylinder 2 disposed within an outer tube or cylinder 1, said inner cylinder being slidably engaged with said outer cylinder. Thus, the inner cylinder 2 can be axially moved relative to the outer cylinder 1. The inner cylinder is further provided with forceps tongs 3 (grasping means), axially disposed therein. The outer cylinder is provided with an operating slide 4, which through the use of a connecting means such as locking set screw 5 is placed in operative engagement with the outer cylinder, the inner cylinder and the forceps tongs. The proximal end of the ring applicator is provided with a thumb ring 6 which is adapted to receive the thumb of the physician. The ring applicator is disposed in an operating channel provided in a laparoscope where it is fixed in its position. The lens system of the laparoscope 17 is offset from the main operating channel which houses the ring applicator device in order to avoid the possible contamination of the physician's hand with the face of the operator. Also, the forceps tongs 3 can be canted from the axial direction of the ring applicator device so that when the physician is looking through the laparoscope it is ensured that the forceps tongs are visible through the laparoscope optics.

FIG. 2 shows the ring applicator device and laparoscope of FIG. 1 in a disassembled state. The inner cylinder 2 is provided with a slot 7 and the outer cylinder 1 is provided with a slot 8, the slot 8 in the outer cyinder being longer than the slot 7 in the inner cylinder. In its assembled state, the locking screw 5 which contains a stem 9 is screwed into a hole 10 provided in the operating slide 4, the stem 9 extending through the slot 8 in the outer cylinder and the slot 7 in the inner cylinder and into the hole 11 provided in the shaft portion 12 of the forceps tongs 3. The ring applicator device of the present invention is combined with an endoscopic system such as, for example, a laparoscope. The laparoscope 17 contains an operating channel 18 which is adapted to receive the ring applicator device. An engaging member 19 disposed on the outer cylinder of the ring applicator device and an applicator lock 20 disposed on the operating channel of the laparoscope are utilized to fix the ring applicator device to the operating channel of the laparoscope. The light source for the laparoscope is introduced through conduit 21.

Figure 3A:
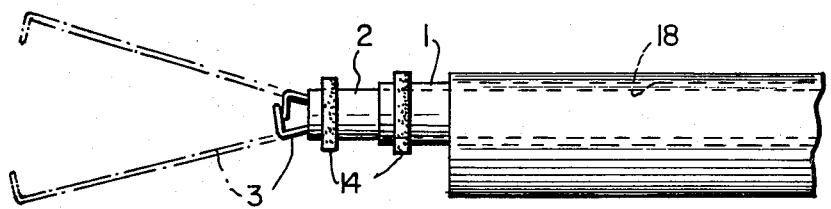
FIGS. 3A to 3G show, in a sequence of steps, the cooperation of the ring applicator device with the laparoscope in effecting the multiple ring application as defined by the method and apparatus of the present invention.

FIGS. 3A to 3G show the multiple ring applicator device of the present invention in its operation as it combines with the proximal end portion of the laparoscope. Thus, when the operating slide 4 is moved from a position where the forceps tongs are extended from the distal end of the ring applicator device toward the distal end of the ring applicator device, the stem 9 which is in an engaging relationship with the hole 11 pulls the forceps tongs containing a Fallopian tube into a position inside the proximal end of the inner cylinder of the ring applicator device as shown in FIG. 3A.

Figure 3B:
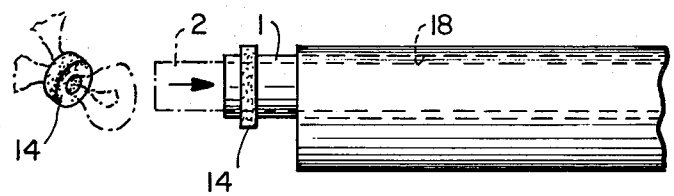

During this initial operation, since the stem of the locking screw slides through the slots 7 and 8 of the inner and outer cylinders, respectively, said cylinders do not move relative to each other. However, as the operating slide is continually moved toward the distal end of the ring applicator device, the stem 9 will eventually engage the end of the slot 7 of the inner cylinder and thus the inner cylinder will be moved in the rearward direction by the stem 9, thereby compressing the spring 13 and causing the inner cylinder 2 to move inside of the outer cylinder 1 as shown in FIG. 3B which displaces the elastic ring 14 from the proximal end of the ring applicator device. The sliding of the operating slide in the rearward direction will be concluded when the stem 9 engages the end of the slot 8 in the outer cylinder. Thus, the grasping of a reproductive tubular member and drawing it into a knuckle inside of the ring applicator device and the release of the elastic ring around said knuckle is effected through a single manipulation of the ring applicator device, that is, by merely sliding the operating slide with the fore and middle fingers to the rear of the ring applicator device. When the ring applicator device is assembled, the knurled nut 15 is in engaging relationship with the threaded portion 16 which is adjacent to the thumb ring 6. Then the operating slide is moved in the proximal direction of the instrument, thereby extending the forceps tongs from the proximal end of the inner cylinder and releasing the Fallopian tube which has been occluded by the elastic ring 14, as shown in FIG. 3B.

Figure 3C:
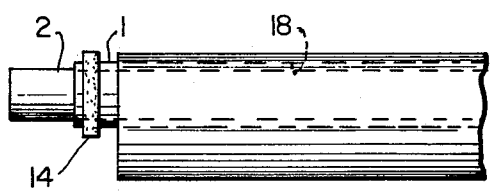
Figure 3D:
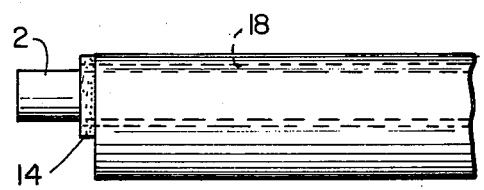
Figure 3E:
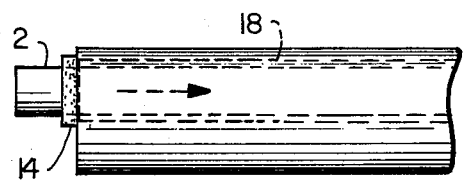
Figure 3F:
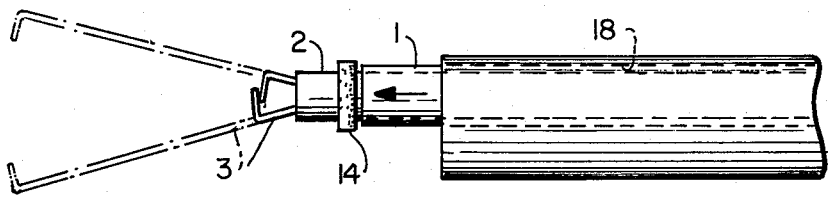
Figure 3G:
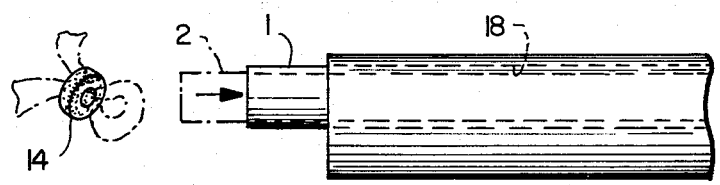

The operating channel of the laparoscope is provided at its proximal end with an applicator lock 20 which can more accurately be defined as a female collar containing internal screw threads. On the other hand, the outer cylinder of the ring applicator device is provided with an engaging member 19 which might more accurately be defined as a male collar containing external screw threads. The male collar containing the external screw threads is fixed in position to the outer cylinder of the ring applicator but rotatably disposed with respect thereto. Thus, when the screw threads of the male collar are placed into screw engagement with the screw threads of the female collar, the ring applicator can be moved into and out of the operating channel of the laparoscope, thereby moving the proximal end of the outer and inner cylinders of the ring applicator device relative to the proximal end of the laparoscope. Generally speaking, the length of the male and female screw threads determine the length of the relative movement which can be made between the ring applicator device and the laparoscope. Thus, assuming that the ring applicator device is disposed in the operating channel 18 of the laparoscope and is fixed in its position by the screw engagement of the male collar 19 with the female collar 20, the reloading of the instrument as shown in FIGS. 3C to 3E can be achieved without removing the instrument from the patient by unscrewing the male collar disposed on the outer cylinder of the ring applicator device from the female collar disposed on the operating channel of the laparoscope, thereby moving the ring applicator device relative to the operating channel of the laparoscope and thus retracting the distal end of the inner and outer cylinders into the operating channel relative to the proximal end of the laparoscope. Thus, in the sequence shown in FIGS. 3C to 3E, the inner and outer cylinders of the ring applicator device are moved axially in the proximal direction until the elastic ring is eventually pushed by the proximal end of the laparoscope from the outside cylinder onto the inside cylinder. Once the exchange of the elastic ring from the outside cylinder to the inside cylinder has been effected as shown in FIG. 3E, the male collar is then placed into full screw engagement with the female collar, thereby extending both the inside and outside cylinders beyond the proximal end of the laparoscope as shown in FIG. 3F. Now the physician is ready to ligate the second Fallopian tube by moving the operating slide in the proximal direction thereby drawing the Fallopian tube into a knuckle inside of the inner cylinder and displacing the elastic ring from the inner cylinder to a position around the bent Fallopian tube in a single operative step. The operating slide can then be moved in the forward direction to release the Fallopian tube which has now been ligated by the elastic ring as shown in FIG. 3G.

In another embodiment of the present invention, the male and female screw mechanisms referred to above can be replaced by a spring and latch mechanism. Thus, a latch means is provided for locking the outer cylinder to the operating channel of the laparoscope. Also, the spring can be attached to either the operating channel of the laparoscope or to the outer cylinder. Thus, by unlocking the outer cylinder from the laparoscope the force of the spring will pull the outside cylinder into the operating channel of the laparoscope, thereby displacing the ring from the outside cylinder to the inside cylinder in a similar manner as is achieved by the male and female collars. After the reloading operation has been concluded, the spring is then compressed and the ring applicator device is locked into position within the operating channel of the laparoscope.

Incidentally, the male collar 19 disposed on the outer cylinder is advantageously provided with an extended lip 22 which facilitates the engagement of the male collar 19 into the female collar 20. It is readily apparent that the male and female screw mechanisms can be reversed on the respective ring applicator device and laparoscope.

As shown in FIG. 2, the metal locking screw 5 can be provided with a metal cap 23 which is connected to a source of electrical current. Thus, by electrically charging the cap 25, electrical current is transmitted through the locking screw 5, the stem 9, the shaft 12 and finally, the forceps tongs 3. In such an installation, it would be necessary to insulate the stem 9 where it passes through the operating slots 7 and 8 so that the inner and outer cylinders are completely insulated from the electrical charge. Alternatively, the inner and outer cylinders can be made of a nonelectrically conductive plastic material and thus the electrical current would only be transmitted to the metal shaft 12 and the metal forceps tongs 3. As previously stated, such an addition to the ring applicator device of the present invention substantially increases its flexibility in that once the physician has introduced the instrument into the patient, he could conduct other medical procedures which would require an electrical current without removing the instrument from the patient.

FIGS. 4A and 4B show further embodiments of the forceps tongs when it is desired to sever and cauterize the Fallopian tubes through the use of an electrical current. Thus, the forceps shown in FIGS. 4A and 4B have been modified slightly so that the ends of the forceps tongs abut against each other to facilitate the operative procedure.

The sterilization operation utilizing the ring applicator device as defined by the present invention renders sterilization so simple that only about 5 to 10 minutes are required to perform the operation and, accordingly, an out-patient procedure may be employed where permitted. This is particularly important in developing countries where hospital facilities are not abundant and may not even be available.

A particular advantage of the present invention is that the blockage of the tubes can be made permanent or temporary, as desired. This particular feature of the invention depends upon the size and the elastic power of the rings employed. If the rings are very small and have a strong elastic power, they will so tightly grip the Fallopian tubes that the blood supply in this part of the tube will be completely blocked, thereby resulting in a sluffing off of the knuckle formed in the tube to effect a permanent sterilization. However, if the elastic bands are of a larger size and/or have a smaller elastic power, it is possible to effect a temporary or reversible sterilization since, although the elastic band will serve to prevent the ovum passage to the uterus, the holding power thereof will not be so strong as to shut off the blood supply through the walls of the Fallopian tubes. In this situation, the knuckle formed in the tubes will remain and will not sluff off. Accordingly, if the woman should desire to return to a normal situation at a later time, it would be possible for the Fallopian tubes to be restored to their natural function by merely removing the elastic rings. Hence, the results of permanent or temporary sterilization are dependent upon the size of the rings used and/or the elastic power thereof.

The rings used for application to the Fallopian tubes are made of government-approved, non-tissue reactive material which has a strong enough elastic power to perform the function described herein. Various rubbery materials may, of course, be used. The preferred material is silicone rubber, for example, the material commercially available under the name "Silastic". Collagen or any other absorbable or nonabsorbable synthetic elastic material which is not harmful to human tissue may be employed, for example, latex rubber or Teflon (tetrafluoroethylene). As pointed out above, the size of the rings may also be varied wherein smaller rings are used for permanent tubal ligation, and larger rings are used in connection with effecting a temporary sterilization. Spring-like metal rings, preferably made of stainless steel, can also be used, as discussed above.

The device of the present invention can be made of medically-approved materials, including many different types of metals, preferably stainless steel, plastics and the like and, hence, is relatively inexpensive because of its simple nature. It can also be made as a disposable instrument, for example, from a synthetic resin such as polyethylene, polypropylene, polycarbonate, polystyrene, polyamide, polyacetate, or acrylic resin. In this embodiment, the wall of the ring applicator can itself act as a laparoscope for transmitting the light from a light source to the internal cavity, and a tube can be disposed around the inner cylinder (which would have a needle-like point) to push an elastic ring over the salpinx portion of the Fallopian tube when it is slid or otherwise moved with respect to said inner cylinder. This embodiment of the invention would be especially attractive where inexpensive instruments are a necessity. Moreover, the ring applicator device of the present invention has a wide range of applicability since it can be used in conjunction with the regular abdominal laparoscopic technique, as discussed above, or in connection with the known vaginal culdascopic procedure. In this latter procedure, the instrument of the present invention can be curved. The use of the device eliminates the need for large, bulky equipment which is normally used with the electrical procedures employed in the prior art as well as the complicated carbon dioxide supply systems used with other techniques. A very simple and relatively small carbon dioxide supply system can be used together with the instrument, or a squeeze bulb may be used to provide the necessary gas and to maintain the required gas pressure inside the abdominal cavity while the operation is being performed. The elimination of complicated electrical and gas supply systems makes it possible to save time in setting up for the procedure. In addition, as pointed out above, the operation may be carried out quite quickly, in less than 10 minutes.

It is understood that various specific mechanical embodiments may be employed to perform the various functions described herein. Basically, the invention comprises an instrument for puncturing and entering into the body cavity, grasping the Fallopian tubes, slipping an elastic ring thereover, and optionally cutting the tubes, if desired. The associated equipment represents technical modifications and adds to this basic idea, and a particularly preferred embodiment is the use of the ring applicator of the invention together with the laparoscope or a similar viewing instrument.

As can be readily recognized, any optical endoscopic system can be utilized, for example, laparoscopes, culdoscopes, and hysteroscopes, in conjunction with the ring applicator device of the present invention. Thus, the particular endoscope must be modified so that it can be physically combined with the ring applicator device of the present invention.

In an analogous manner, the method and device of the present invention may be used to effect the sterilization of the human male. In this case, the appropriate incision is made and one or more elastic rings are applied to the vas to effect the ligature thereof and block the passage of the sperm. The elastic or stretchable rings used in this connection must, of course, be small enough to ligate the small diameter of the vas.

The single-action operation of the ring applicator device of the present invention can be accomplished in a number of ways other than the particular embodiment disclosed in the drawings. For example, the ring applicator device can be the same as shown in the drawings except that the inner cylinder can be substantially shortened in length so that it is disposed only in the front-end portion of the device. However, the relationship of the inner and outer cylinders and the laparoscope at said front-end portion remains the same. In this instance, the spring mechanism is also relocated to the front of the instrument, behind the inner cylinder where it is fixed in position. The grasping forceps which still extends coaxially, substantially the entire length of the instrument, is provided with a collar disposed behind the grasping forceps which, as it is drawn in the rearward direction engages the rear end portion of the inner cylinder. At this instant the grasping forceps containing the Fallopian tube has been withdrawn into the inner cylinder. By continuing the rearward pull of the operating slide (which is attached to the shaft of the grasping forceps), the inner cylinder is pulled in the rearward direction which, in turn, compresses the spring causing the displacement of the inner cylinder relative to the outer cylinder and the resulting displacement of the ring from the inside cylinder. In this arrangement, since the inner cylinder is restricted to the front portion of the device, only one operating slot is necessary which is disposed in the outside cylinder. The screw element of the operating slide thus extends through said slot into engaging relationship with the shaft of the grasping forceps.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

It is claimed:

1. An instrument for applying multiple elastic occluding rings to anatomical tubular structures without the necessity of reloading the instrument which comprises a ring applicator device combined with an endoscope, said ring applicator device comprising an inner cylinder and an outer cylinder, said inner cylinder being slidably disposed within said outer cylinder, forceps means slidably disposed within said inner cylinder and operating slide means operatively associated with the forceps means and the inner and outer cylinders for sequentially displacing the forceps means in the proximal direction relative to the inner and outer cylinders and for displacing the forceps means and inner cylinder in the proximal direction relative to the outer cylinder as the result of a single movement of said operating slide means toward the proximal end of the instrument, said ring applicator device being combined with said endoscope so that the distal end portion of the ring applicator device extends beyond the distal end portion of the endoscope, and engaging means provided with the ring applicator device and the endoscope, said engaging means cooperating to produce relative movement between the ring applicator device and the endoscope in the axial direction of the instrument for displacing an elastic occluding ring from the outer cylinder to the inner cylinder at the distal end of the ring applicator device.

2. The instrument of claim 1, wherein the endoscope is a laparoscope provided with an operating channel and an optical viewing means, said operating channel housing the ring applicator device and said optical viewing means being offset from said operating channel and the ring applicator device disposed therein.

3. The instrument of claim 2, wherein the engaging means for the ring applicator device comprises a first screw mechanism and the engaging means for the laparoscope is a second screw mechanism, said first and second screw mechanisms being in screw engagement with each other so that by gradually disengaging the first and second screw mechanisms the ring applicator device and the laparoscope can be axially displaced relative to each other.

4. The instrument of claim 2, wherein the engaging means for the ring applicator device is a male screw mechanism and the engaging means for the laparoscope is a female screw mechanism, said female screw mechanism being disposed at the proximal end portion of the operating channel of the laparoscope.

5. The instrument of claim 2, wherein the engaging means for the ring applicator device and the laparoscope is a spring-and-latch mechanism.

6. The instrument of claim 1, wherein the distal end portion of the inner cylinder extends beyond the proximal end portion of the outer cylinder which, in turn, extends beyond the distal end portion of the endoscope.

7. The instrument of claim 1, wherein connecting means provide communication between the operating slide means and the forceps means independent of the inner and outer cylinders, said forceps means thereby being capable of independent movement in both the proximal and distal directions relative to the inner and outer cylinders.

8. The instrument of claim 7, wherein the inner cylinder is provided with a means for engaging the connecting means independent of the outer cylinder, said inner cylinder thereby being capable of independent movement in the proximal direction relative to the outer cylinder.

9. The instrument of claim 8, wherein the forceps means contain a shaft portion and the inner and outer cylinders are provided with first and second operating slots, respectively, said connecting means extending through said first and second operating slots and into engaging relationship with said shaft position.

10. The instrument of claim 9, wherein the first operating slot is shorter than said second operating slot and the means for engaging said connecting means is the proximal end of the first operating slot.

11. The instrument of claim 10, wherein the first operating slot is shorter than said second operating slot and extends to the proximal end of the inner cylinder, and the means for engaging said connecting means is said proximal end of the inner cylinder.

12. The instrument of claim 1, wherein a spring means is attached to the proximal end portion of the inner cylinder, said spring means being compressed by the movement of the forceps means and the inner cylinder in the proximal direction relative to the outer cylinder.

13. The instrument of claim 1, wherein an optical viewing means and an illuminating means are combined with the ring applicator device.

14. The instrument of claim 1, wherein the endoscope is a culdoscope.

15. The instrument of claim 1, wherein the endoscope is a hysteroscope.

16. The instrument of claim 1, wherein the forceps means are canted from the axial direction of the ring applicator device.

17. An instrument for applying multiple elastic occluding rings to reproductive tubular members without the necessity of reloading the instrument which comprises a ring applicator device combined with a laparoscope containing an operating channel and an optical viewing means, said ring applicator device comprising an inner cylinder provided with a first operating slot and an outer cylinder provided with a second operating slot which is longer than said first operating slot, said inner cylinder being slidably disposed within said outer cylinder, forcep means slidably disposed within said inner cylinder, said forceps means containing a shaft portion which has an engageable end portion, and an operating slide means disposed on said outer cylinder, said operating slide means provided with connecting means which extends from the operating slide, through said first and second operating slots and into engaging relationship with said engageable end portion, said ring applicator device being disposed in the operating channel of the laparoscope so that the distal end portion of the ring applicator device extends beyond the distal end portion of the laparoscope, and engaging means provided with the ring applicator device and the operating channel of the laparoscope, said engaging means cooperating to produce relative movement between the ring applicator device and the laparoscope in the axial direction of the instrument for displacing an elastic occluding ring from the outer cylinder to the inner cylinder at the distal end of the ring applicator device.

18. The instrument of claim 17, wherein said operating slide means has a forward extended position determined by contact between said connecting means and the distal end of said second operating slot, and wherein when the operating slide means is in said forward extended position the distal end portion of the inner cylinder extends beyond the distal end portion of the outer cylinder and the forceps means extends from the end portion of the inner cylinder.

19. The instrument of claim 18, wherein the proximal ends of the first and second slots are in alignment so that as the operating slide means is drawn toward the proximal end of the device, the forceps means is drawn into the inner cylinder and the connecting means engages the rear end portion of the first operating slot which moves the inner cylinder in the proximal direction relative to the outer cylinder.

20. The instrument of claim 17, wherein the engageable end portion of said shaft is an aperture and the connecting means is a set screw which extends from the operating slide means through the first and second operating slots and into screw engagement with said aperture.

21. The instrument of claim 20, wherein a thumb ring is provided at the proximal end of the device.

22. The instrument of claim 21, wherein a spring is provided between the thumb ring and the proximal end of the inner cylinder.

23. The instrument of claim 17, wherein the forceps means are spring-loaded so that they spring open when they are displaced from the end of the inner cylinder.

24. A method of applying multiple elastic occluding rings to reproductive tubular members to effect at least temporary sterilization using a ring applicator device of the type having an inner and outer cylinder wherein a single, hand-initiated manipulation of the device causes a knuckle to be formed in a tubular member and an elastic ring to be applied around the knuckle from the inner cylinder, the ring applicator combined with an endoscope, without the necessity of reloading the instrument which comprises loading each of the outer and inner cylinders with an elastic ring, forming a knuckle in a first reproductive tubular member and applying the inner cylinder elastic ring from the inner cylinder around said knuckle, displacing the outer cylinder elastic ring from the outer cylinder to the inner cylinder by moving the ring applicator device relative to the endoscope, and then forming a knuckle in a second reproductive tubular member and applying the outer cylinder elastic ring from the inner cylinder around said knuckle.

25. The method of claim 24, wherein the ring applicator is moved in the proximal direction relative to the endoscope.

* * * * *

UNITED STATES PATENT AND TRADEMARK OFFICE
CERTIFICATE OF CORRECTION

PATENT NO. : 4,103,680

DATED : August 1, 1978

INVENTOR(S) : In Bae Yoon

It is certified that error appears in the above–identified patent and that said Letters Patent are hereby corrected as shown below:

Column 10, Claim 6, line 68, continuing onto Column 11, line 1, change "proximal" to --distal--.

Signed and Sealed this

Twenty-ninth Day of May 1979

[SEAL]

Attest:

RUTH C. MASON
Attesting Officer

DONALD W. BANNER
Commissioner of Patents and Trademarks